United States Patent [19]

Katsunuma

[11] 4,278,593

[45] Jul. 14, 1981

[54] GLUCOCORTICOID SPARING FACTOR AND PROCESS FOR THE PRODUCTION OF THE SAME

[76] Inventor: Nobuhiko Katsunuma, No. 1-78, Shomachi, Tokushima-shi, Tokushima-ken, Japan

[21] Appl. No.: 109,095

[22] Filed: Jan. 2, 1980

[30] Foreign Application Priority Data

Jan. 11, 1979 [JP] Japan .................................... 54-2566

[51] Int. Cl.³ .......................... C12P 21/00; C07G 7/00
[52] U.S. Cl. ................................... 260/112 R; 435/68; 435/822; 435/847; 435/849; 435/852; 435/873; 435/879; 435/881; 435/89; 424/115

[58] Field of Search ........................... 435/89, 68, 170; 424/115; 260/112

[56] References Cited

U.S. PATENT DOCUMENTS 3,928,568  12/1975  Katsunuma .................... 435/68 X
4,229,571  10/1980  Katsunuma .................. 435/170 X

*Primary Examiner*—Lionel M. Shapiro
*Attorney, Agent, or Firm*—Browdy and Neimark

[57] ABSTRACT

A glucocorticoid sparing factor (GSF) which amplifies liver enzyme induction which is caused in glucocorticoid and a process for the production of GSF are disclosed. GSF can be isolated from the culture broth of a microorganism of the Family Enterobacteriaceae.

8 Claims, 1 Drawing Figure

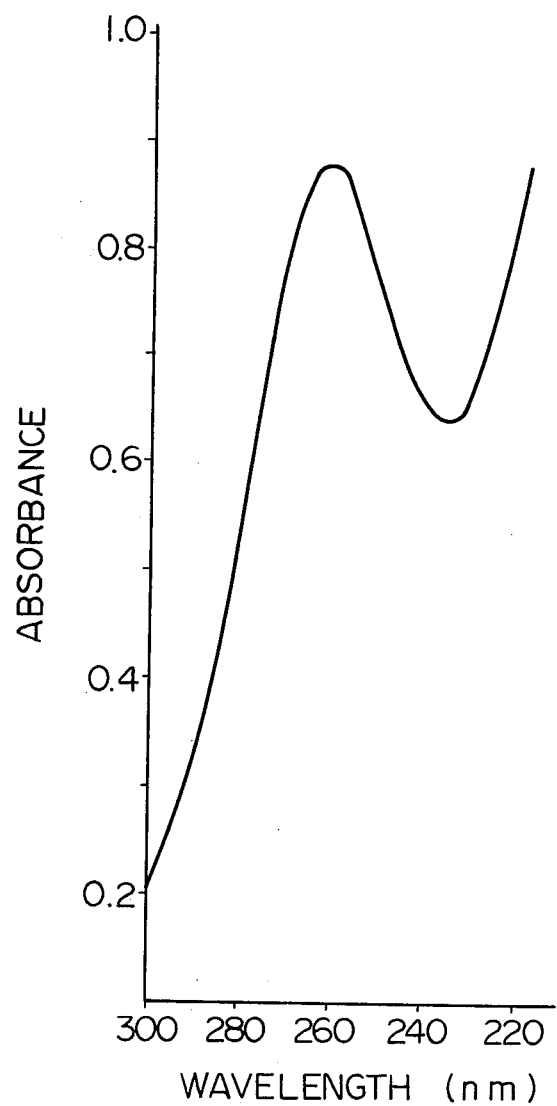

GLUCOCORTICOID SPARING FACTOR AND PROCESS FOR THE PRODUCTION OF THE SAME

This invention relates to a substance amplifying the activities of glucocorticoid and a process for the production of said substance.

The inventor of this invention succeeded in isolating a peptide which amplifies the induction of tyrosine transaminase, as a product from a microorganism of the Family Enterobacteriaceae, such as *Proteus mirabilis*. Thereafter, the inventor continued his study on the influence of metabolic substances from *Proteus mirabilis* upon the various enzymes, and found a novel uridine derivative which amplifies liver enzyme induction which is caused by glucocorticoid in the metabolic product. The uridine derivative is referred to as glucocorticoid sparing factor or GSF hereunder.

Thus, this invention relates to GSF and to a process for the production of the same.

In accordance with this invention, GSF is produced by a process which comprises cultivating a microorganism of the Family Enterobacteriaceae under the conventional cultivating conditions, recovering bacterial cells by centrifugation or filtration, extracting bacterial substances, for example, by sonic destruction of the cells and, after deprotenization, treating the extract with activated charcoal. The object substance adsorbed on the surface of activated charcoal is then eluted with proper liquid such as alkali-acetone mixture or a 10–30% aqueous ethanol and purified by appropriate purification such as gel filtration, column chromatography on an ion exchanger or paper chromatography to obtain a purified object substance. The substance may be lyophilized for long term storage. The microorganism of the Family Enterobacteraceae which are employed according to this invention are those microorganisms belonging to the genera of Escherichia, Aerobacter, Klebsiella, Paracolobactrum, Alginobacter, Erwinia, Serratia, Salmonella, Proteus and Shigella. Examples of the species include *Escherichia coli*, *Erwinia aroidaae*, *Erwinia carotovora*, *Serratia marcescens*, *Proteus mirabilis*, *Proteus vulgaris*, *Proteus morganii*, *Aerobacter aerogenes* and the like. All of them are well-known and easily available microorganisms of the Family Enterobacteraceae.

The filter mediums which are useful in the gel filtration in accordance with this invention include, for example, Sephadex G and Sephadex LH-20 (manufactured by Pharmacia Fine Chemicals AB, Sweden) and Polystyrene gel G 3000S (manufactured by Toyo Soda Kabushiki Kaisha, Japan). The ion exchangers which are useful for the column chromatography of this invention include, for example, ion exchange celluloses such as diethylaminoethyl (DEAE) cellulose or ion exchange resins such as Dowex type ion exchange resin.

The thus obtained GSF is a substance having the following physical and chemical properties:

a. Colorless and acidic;
b. Easily soluble in water and in a diluted aqueous acid or alkali;
c. Positive to 1,10-phenanthroline reaction and Anthrone reaction; Negative to Folin-Thiocalt reaction and Elson-Morgan reaction;
d. Ultraviolet absorption spectrum is as shown in FIG. 1 wherein a peak is seen at 260 nm;
e. Molecular weight is presumed to be between about 400 and 1,000, calculated from the elution curve obtained with the use of Sephadex G-25 (manufactured by Pharmacia Fine Chemicals AB, Sweden);
f. Rf is about 0.51 as measured by ascending method using filter paper, preferably, Toyo Filter paper No. 526 (Toyo Roshi Kabushiki Kaisha, Japan) and isopropanol-aqueous ammonia-water (7:1:2 v/v) as a developing agent; and
g. Having uracil, pentose, hexose and phosphate radical which can be easily hydrolyzed by the action of acids.

Aside from the above physical and chemical properties, GSF has the following biological properties:

1. GSF indicates in vivo an amplifying action on the induction of tyrosine transaminase and leucine transaminase by glucocorticoid (triamcinolone or dexamethasone) in liver of adrenalectomized rat.

2. In case an adrenalectomized rat is administered GSF alone, the induction of liver tyrosine transaminase is not influenced by the administration.

3. GSF does not influence the induction of liver tyrosine transaminase of rat by glucagon or insulin.

4. GSF indicates an amplifying action on the induction of the tyrosine transaminase by glucocorticoid in in vitro system using liver of adrenalectomized rat under the perfusion method, when GSF is added to the system prior to or at the same time as the administration of glucocorticoid.

5. The addition of GSF indicates an amplifying action on the induction of tyrosine transaminase in a tissue-culture of liver cancer cells 7288.

6. If GSF receives the action of α-glucosidase and phosphodiesterase II, all of the biological activities enumerated above are lost. In contrast, the activities of GSF are not affected at all by the action of any one of α-amylase, neuraminidase, hyaluronidase, lysozyme, chymotrypsin, trypsin, pepsin, proteinase, papain, collagenase, aminopeptidase M, carboxypeptidase A and B, leucine-aminopeptidase, deoxyribonuclease 1, ribonuclease $T_1$ +A, acid phosphatase and alkali phosphatase.

7. GSF is completely deactivated to form reducing sugar if it is heated in a 6 N hydrochloric acid at 105° C. for 12 hours. On the other hand, it is not deactivated for 48 hours in a buffer solution having a pH of 4.2–9 at 37° C.

As mentioned above, GSF according to this invention has a strong amplifying action on enzyme induction caused by glucocorticoid, and, therefore, it is useful for treatment of various diseases which have been objects for medication of glucocorticoid, such as lymphatic leukemia, diffuse collagen disease or infectious disease.

The drawing is a chart of ultraviolet light absorption spectrum of GSF according to this invention. In the chart, the vertical axis shows absorbance and the horizontal axis shows the wave length.

This invention is further illustrated by the following Examples and Experiments.

EXAMPLE 1

Cells (20 kg) of the microorganism, *Proteus mirabilis* (ATCC 21718), were suspended in physiological saline solution in twice the volume of the cells, and the suspension was centrifuged at 8,500 G for 10 minutes to collect the cells. After repeating the washing, the cells were suspended in a 2.8% aqueous perchloric acid solution in an equal volume of the cells and sonicated under ice-cooling with Kubota Model 200μ sonic generator at 180 W for 7 minutes to rupture the cells. After the addition of a 2.8% aqueous perchloric acid solution in an amount three times the volume of the sonicated liquid in order to accelerate the precipitation, the sonicated liquid was centrifuged at 8,500 G for 10 minutes. The supernatant was charged through a column (6×30 cm) filled with activated charcoal (column chromatography grade: Wako Junyaku K.K., Japan) at a proportion of 50 g (dry basis) per every one liter, washed with 0.1 N hydrochloric acid and eluted with 10% aqueous ethanol and then 30% aqueous ethanol. The fraction eluted the 30% aqueous ethanol, which indicated activities was chromatographed with a column (2.5×60 cm) filled with Sephadex LH-20, and eluted with n-butanol-pyridine-water (1:1:20). A fraction of eluate having the activities was chromatographed using a column (6×30 cm) filled with Polystylene gel G3000S and eluted with distilled water to collect the eluate. The eluate was concentrated and chromatographed with Toyo Filter Paper No. 526 (Toyo Roshi Kabushiki Kaisha, Japan) using isopropanol-aqueous ammonia-water (7:1:2 by volume) as a developing agent by an ascending method to give a spot having an RF Value of about 0.51 and an absorption in ultraviolet region. The portion of the paper having the spot was cut out and eluted with distilled water. After concentration of the eluate, it was chromatographed again with Toyo Filter paper No. 526 (Toyo Roshi Kabushiki Kaisha, Japan) using 0.5 M ammonium acetate in ethanol (pH 3.8) as a developing agent by an ascending method. The portion having an Rf of about 0.22 and an absorption in ultraviolet region was cut out of the filter paper and eluted with distilled water, and the eluate concentrated. The concentrate was chromatographed with a column (2.0×23 cm) filled with Dowex 1 (Cl⁻ type) and the fraction eluted with 0.003 N hydrochloric acid containing 0.4 M sodium chloride was collected and lyophilized to give an object substance.

EXAMPLE 2

Wister strain male rats weighing 120–140 g were adrenalectomized and glutted with CE-2 type of solid food (manufactured by Clea Japan Inc., Japan) and with physiological saline as water supply for 5–7 days. The rats which were divided into group of 4 members each were intraperitoneally administered dexamethasone alone in a dose of 0.2–100 $\mu$g/100 g body weight, or dexamethasone (0.2–100 $\mu$g/100 g) plus GSF (0.25 $\mu$g/100 g). Nine hours after the administration, the rats were sacrificed and the activities of tyrosine transaminase in their livers were determined.

The determination of the activities was made in the manner of Rosen et al., reported in J.B.C. Vol. 238 (1963) pp. 3725–3729, and an amount of enzyme such that 1$\mu$ mole of p-hydroxyphenylpyruvic acid is formed per minute was defined as one unit.

As the results of the determination, the administration of one $\mu$g of dexamethasone alone indicated activities of tyrosine transaminase comparable to those obtained in case no reagent was administered. Whereas, in case GSF (0.25 $\mu$g) was administered in addition to dexamethasone (1 $\mu$g), the enzyme induction was extremely amplified to a level which corresponds to that of the administration of about 5 $\mu$g of dexamethasone alone. Incidentally, the administration of GSF alone did not affect the enzyme induction.

EXAMPLE 3

A culture medium (500 ml) containing 1.5% of pepton, 0.5% of yeast extract, sodium chloride (0.5%), glucose (0.25%), and 0.25% of dipotassium phosphate and having a pH of 7.3 was inoculated with each of the different microorganisms listed hereunder. After shaking cultivation at 27° C. for a whole day, the cells were treated as in Example 1 to give purified object substance.

The substance was subjected to Rosen et al method as mentioned above to determine activities of the induction on tyrosine transaminase.

Activities of induction on the enzyme are shown in Table in terms of an average of five measurements per physiological saline (control) being 1.

TABLE

| Microorganism | | | Yield[*1] | Activity of Induction on tyrosine transaminase |
|---|---|---|---|---|
| Aerobacter aerogenes | IAM[*2] | 1183 | 10 (1.87) | 1.63 |
| Aerobacter cloacae | IAM | 1064 | 10 (3.06) | 1.76 |
| Escherichia coli | IAM | 1132 | 10 (5.74) | 2.57 |
| Erwinia aroideae | IAM | 1068 | 10 (4.69) | 1.63 |
| Erwinia carotovora | IAM | 1024 | 10 (3.18) | 1.89 |
| Serratia marcescens | IAM | 1023 | 10 (2.14) | 1.95 |
| Proteus mirabilis | OM-3[*3] | (ATCC 21721) | 10 (3.43) | 2.18 |
| Proteus mirabilis | N-3 | (ATCC 21720) | 10 (5.51) | 2.70 |
| Proteus morganii | AA-2[*3] | | 10 (3.49) | 2.41 |
| Proteus vulgaris | YO-5[*3] | | 10 (4.42) | 2.82 |

Remarks
[*1]GSF Volume (ml) and (absorbance at 260 nm)
[*2]Inst. of Appl. Microbiol, Tokyo Univ.
[*3]Reference number of Research Institute for Chemobiodynamics Chiba University, Chiba-ken, Japan.

What is claimed is:

1. A glucocerticoid sparing factor characterized in that:

it is a colorless and acidic substance produced in a culture broth of a microorganism of the Family Enterobacteriaceae;

it has a molecular weight between about 400 and about 1,000;

it is a uridine derivative having uracil, pentose, hexose and phosphate radical which can be easily hydrolyzed by the action of acids;

it amplifies the liver enzyme induction, with said amplifying action being deactivated by the action of $\alpha$-glucosidase and phosphodiesterase II, but not being affected by the action of $\alpha$-amylase, neuraminidase, hyaluronidase, lysozyme, chymotripsin, trypsin, pepsin, proteinase, papain, collagenase, aminopeptidase M, carboxypeptidases A and B, leucine-aminopeptidase, deoxyribonuclease 1, ribonuclease $T_1 + A$, acid phosphatase or alkali phosphatase;

it is stable for more than 6 months at $-20°$ C.;

it is stable for minimum of 48 hours in a buffer solution having a pH of 4.2–9 at 37° C.;

it is deactivated to form reducing sugar when heated at 105° C. for 12 hours in 6 N hydrochloric acid;

it has a peak at 260 nm in the ultraviolet absorption spectrum; and it has an Rf of about 0.51 as measured by ascending method using filter paper and isopropanol-aqueous ammonia-water (7:1:2 v/v) as a developing agent.

2. A process for the production of the glucocorticoid sparing factor according to claim 1 which comprises cultivating a microorganism of the Family Enterobacteriaceae and isolating said factor from the bacterial cells.

3. A process for the production of the glucocorticoid sparing factor according to claim 1 which comprises cultivating a microorganism of the Family Enterobacteriaceae, extracting the bacterial substance from the propagated cells by destructing said cells, deproteinizing the extract, causing the extract to be adsorbed on activated charcoal, eluting the adsorbate with an organic solvent-containing solution, and purifying the eluate with gel filtration, column chromatography on ion exchange resin or paper chromatography.

4. A process in accordance with claim 3 wherein said organic solvent-containing solution is selected from the group consisting of 0.2 N aqueous potassium hydroxide-acetone (3:7, v/v) and 10–30% aqueous ethanol.

5. A process in accordance with claim 3 wherein said gel filtration is effected with the use of a filter medium selected from the group consisting of those under the trade names of Sephadex G, Sephadex LH-20 and Polystyrene gel G 3000S.

6. A process in accordance with claim 3 wherein said ion exchange resin for the column chromatography is selected from the group consisting of DEAE cellulose and those under the trade name of Dowex.

7. A process in accordance with claim 3 wherein said microorganism of the Family Enterobacteriaceae is selected from the group consisting of those belonging to the general Escherichia, Aerobacter, Klebsiella, Paracolobactrum, Alginobactor, Erwinia, Serratia, Salmonella, Proteus and Shigella.

8. A process in accordance with claim 3 wherein said microorganism of the Family Enterobacteriaceae is selected from the group consisting of *Escherichia coli, Erwinia aroideae, Erwinia carotovora, Serratia marcesens, Proteus mirabilis, Proteus vulgaris, Proteus morganii* and *Aerobactor aerogenes.*

* * * * *